United States Patent [19]

Bae et al.

[11] Patent Number: 4,931,287

[45] Date of Patent: Jun. 5, 1990

[54] HETEROGENEOUS INTERPENETRATING POLYMER NETWORKS FOR THE CONTROLLED RELEASE OF DRUGS

[75] Inventors: You H. Bae, Salt Lake City, Utah; Teruo Okano, Urayasu, Japan; Sung W. Kim, Salt Lake City, Utah

[73] Assignee: University of Utah, Salt Lake City, Utah

[21] Appl. No.: 206,593

[22] Filed: Jun. 14, 1988

[51] Int. Cl.⁵ ............................................. A61K 9/14
[52] U.S. Cl. .................................. 424/484; 424/78; 424/81; 424/485; 424/486; 424/487; 424/488
[58] Field of Search ............... 424/484, 485, 486, 487, 424/488, 78, 81

[56] References Cited

U.S. PATENT DOCUMENTS

| | | | |
|---|---|---|---|
| 3,641,237 | 2/1972 | Gould et al. | 424/487 X |
| 4,304,591 | 12/1981 | Mueller et al. | 424/486 X |
| 4,605,550 | 8/1986 | Trill | 424/487 |
| 4,681,755 | 7/1987 | Colombo et al. | 424/486 |
| 4,693,887 | 9/1987 | Shah | 424/486 |
| 4,741,872 | 5/1988 | De Luca et al. | 424/486 X |

OTHER PUBLICATIONS

Cowsar et al., ACS Symposium Series 31:180 (1976).
S. C. Kim et al., *J. Appl. Polymer Sci.*, 21:1289 (1977).
R. W. Korsmeyer et al., *Proc. Int. Sym. Contr. Rel. Bioact. Mater.*, 10:141 (1983).
P. I. Lee, *Proc. Int. Sym. Contr. Rel. Bioact. Mater.*, 10:136 (1983).
E. S. Lee et al., *J. Mem. Sci.*, 7:293 (1980).
K. F. Mueller et al., *J. Appl. Polymer Sci.*, 27:4043–4064 (1982).
L. H. Sperling et al., *J. Polymer Sci.*, A-2(7):425 (1969).

Primary Examiner—Thurman K. Page
Attorney, Agent, or Firm—Irell & Manella

[57] ABSTRACT

A heterogeneous interpenetrating polymer network is provided for use in the controlled release of drugs. The network is a heterogeneous matrix that is formed from a hydrophilic component such as polyethylene oxide or poly(N,N'-dimethyl acrylamide-co-styrene) and a hydrophobic component such as styrene, an alkyl methacrylate, or polytetramethylene ether glycol. The relative amounts of the two components, or "domains", can be varied, as can the diffusivities and solubilities of the drug combinations to be loaded therein, to control and change as desired the timed release profile of incorporated drug. Prolonged pseudo-zero order release can be obtained where one domain acts as a diffusion barrier layer to the release of drug from the other domain.

13 Claims, 9 Drawing Sheets

HETEROGENEOUS INTERPENETRATING POLYMER NETWORKS FOR THE CONTROLLED RELEASE OF DRUGS

TECHNICAL FIELD

This invention relates generally to interpentrating polymer networks (IPNs). More particularly, the invention rlates to IPNs useful in the controlled release of drugs, and in which drug release rate can be regulated by the composition of the IPNs.

BACKGROUND

Many ways of preparing and formulating drugs have been developed in order to facilitate gradual release of a drug over time. Conventional "timed release" formulations have typically involved coated tablets which after dissolution of the coating release the entire drug contents of the tablet. Thus, drug concentrations in the blood rapidly reach a peak and then decrease at a rate determined by the metabolic half-life in the body. The need to reshape this profile by eliminating the initial peak, and thus any resulting toxic or other undesirable side effects, has led to the developement of more sophisticated controlled release formulations. In many cases, the desired release pattern is "zero order", i.e., the release rate is approximately constant for most of the drug delivery period.

It has been demonstrated that controlled drug release can be achieved by using a polymer matrix as a drug "reservoir". In general, the drug release rate $Q_t$ (release amount/time) in such devices is proportional to $S \cdot \Delta C/1$, where S is the active surface area; i.e., the area through which drug actually passes (and can be considered as either the area of interface between undepleted and partially depleted regions for solute in the device or the area of membrane that controls overall diffusion rate), $\Delta C$ is the concentration gradient, and 1 is the diffusion length of solute through device. Some drug reservoir devices that have been developed maintain approximately zero order drug release due to constant S, $\Delta C$, and 1.

Geometry considerations can also be introduced in order to control the concentraion profile. For example, as discussed by Lee in *Proc. Int. Sym. Contr. Rel. Bioact. Mater.* 10:136 (1983), drug release can be maintained at an approximately constant rate if $\Delta C/1$ increases as S decreases in drug-loaded polymeric beads.

In addition, zero order release has been obtained using "Case II Diffusion Systems" i.e., where drug diffusion is much faster than polymer relaxation, or swelling ($M_t/M_\infty = kt^n$, where $n=1$, $M_t$ is the total released amount of drug at the time t, and $M_\infty$ is the total released amount of drug at time infinity). Such systems are described, for example, by Lee, supra, and by Korsmeiyer, *Proc. Int. Sym. Contr. Rel. Bioact. Mater.* 10:141 (1983).

Barriers, or release rate controlling membranes, have also been introduced as a way of effecting zero order release. The barrier concept was introduced by Cowsar et al., *ACS Symposium Series* 31:180 (1976), who coated the surface of a hydrogel containing sodium fluoride with a hydrogel having a lower water content. Kim et al., *J. Mem. Sci.* 7:293 (1980), disclosed monolithic devices for the controlled release of progesterone, the devices comprising copolymers of poly(2-hydroxyethylmethacrylate) (pHEMA), poly(methoxyethoxyethyl methacrylate) and/or poly(methoxyethyl methacrylate). The devices were soaked in an ethanol solution of ethylene glycol dimethacrylate (EGDMA), followed by exposure to ultraviolet light to create a crosslinked zone at the outer surface. Devices with such surface barriers can approximate zero order release, where the release rate is controlled by the thickness of the barrier layer and its water content.

The inventors herein now propose the use of an interpenetrating polymer network for use in achieving pseudo-zero order drug release, i.e., a near-constant release rate for a significant portion of the release phase. Other types of drug release profiles, should they be desired, may also be provided using the IPNs disclosed herein. Interpentrating polymer networks have been described in the literature, e.g., by K. F. Mueller and S. J. Heiber, *J. Appl. Polymer Sci.* 27:4043-4064 (1982), S. C. Kim et al., *J. Appl. Polymer Sci.* 5:1289 (1977), and L. H. Sperling and D. W. Friedman, *J. Polymer Sci.* A-2(7): 425 (1969). As described in the Mueller et al. article, in an IPN, one preformed crosslinked polymer matrix actually contains a second polymer which penetrates the matrix throughout but is not covalently bound to it. IPNs may be prepared by either simultaneous or sequential synthesis. In sequential synthesis, a selected monomer is diffused throughout a preformed crosslinked matrix and then polymerized within it. In simultaneous synthesis, the mixture of monomers, prepolymers, linear polymers, crosslinkers, initiators, and the like, for both component networks, form a homogenous fluid. Both components are then simultaneously polymerized and/or crosslinked by independent, noninterfering reactions.

Potential uses of IPNs in drug formulations and in drug delivery in general remain to a large extent undeveloped. The inventors hering now propose the use of heterogeneous IPNs (HTIPNs), i.e., an IPN which contains both hydrophilic and hydrophobic domains, to provide a controlled release drug device such that the degree of drug loading as well as the overall drug release profile can be carefully controlled.

DISCLOSURE OF THE INVENTION

In one aspect, the invention is a drug-containing three-dimensional interpenetrating polymer networks (IPN), comprising a matrix of a first polymeric material; localized regions of a second polymeric material dispersed throughout said matrix, wherein one of said polymeric materials is hydrophilic and the other of said materials is hydrophobic; and a drug either dissolved or dispersed in one or both of said polymeric materials.

In another aspect, the invention is a method for making a drug-containing IPN, comprising polymerizing a first component to give a matrix of a first polymeric material; polymerizing a second component to give an IPN having localized regions of a second polymeric material within said matrix, wherein one of said first and said second materials is hydrophilic and the other of said materials is hydropholic; and incorporating drug in the IPN by immersion in a drug solution. The two polymerization reactions may be carried out either simultaneously or sequentially.

The invention is thus directed to a self-contained, drug release rate-controlling IPN containing two doamins: a first domain of a first polymeric material and a second domain of a second polymeric material, wherein, relative to each other, one of the materials is hydrophilic and the other is hydrophobic. The matrix may be formed by either simultaneous or sequential polymerization of the two materials. Drug release, which is effected via a diffusion mechanism, is primarily dependent on drug permeability in the two materials, which in turn is a function of both drug solubility and diffusivity.

The rate of drug release may be carefully controlled not only by carefully selecting the diffusivities $D_1$ and $D_2$ of the drug in the two polymeric materials and the solubilities $S_1$ and $S_2$ of the drug in the two materials, but also the relative amounts of drug in the two domains, the degree of hydrophobicity and hydrophilicity of the two materials, and the solvent used to load drug. Thus, the device allows for a great deal of flexibility and control.

Other advantages of using such an HTIPN in a drug formulation are as follows. First, drug can be loaded into either or both domains, depending primarily on the solvent selected for the drug loading step. Second, pseudo-zero order release can be obtained if one domain acts as a barrier layer to release from the other domain. Third, delayed burst effects may be obtained, that is, a peak of drug release at some point after release has been gradual and approximately constant for a predetermined period of time. Finally, design and fabrication of delivery systems from such a device is a simple synthetic process, easily adapted to mass production.

MODES FOR CARRYING OUT THE INVENTION

Figure 1:
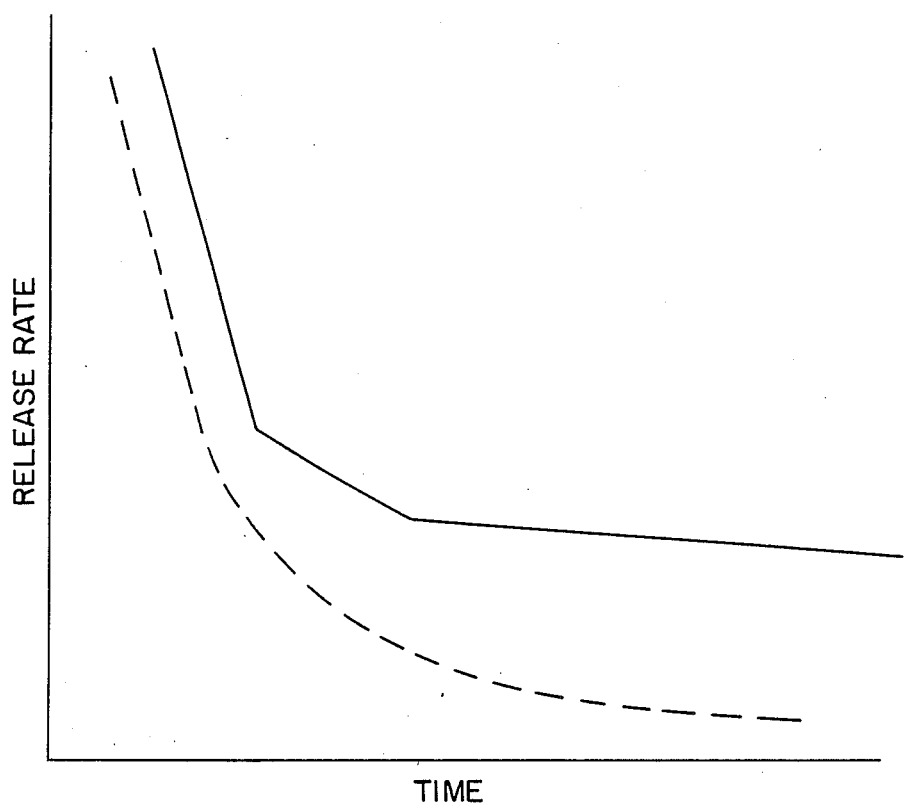
FIG. 1 is a graph showing the predicted release kinetics from the "Case 1" IPNs of the present invention.

In the heterogeneous IPNs of the invention, the domain which represents the matrix or the "continuous phase" comprises a first polymeric material while the domain which represents the localized regions within the matrix, or the "discrete phase", comprise a second polymeric material. One of the polymeric materials is hydrophobic, while the other is hydrophilic. Which of the domains is hydrophobic and which hydrophilic determines to a large extent the release rate and overall release profile of drug from the IPNs. Either or both of the domains can be loaded with a drug in a dissolved or dispersed form, by immersion of the device in a drug solution or dispersion.

MATERIALS

The hydrophilic component is typically a water soluble prepolymer with functional end groups that are crosslinkable with appropriate crosslinking agents such as polyethylene oxide (PEO); any water swellable polymer, which may or may not be crosslinked, such as pHEMA; or any copolymer of water soluble and relatively hydrophobic monomers, which may or may not be crosslinked.

The hydrophobic component is a water insoluble prepolymer such as polypropylene oxide (PPO), polytetramethylene oxide (PTMO) or poly($\epsilon$-caprolactone) having functional end groups crosslinked with appropriate crosslinkers; or any water swellable or unswellable polymers or copolymers with or without a crosslinker as will be described below. Where a water swellable material is used as the hydrophobic component, it is typically and preferably less swellable than the material used as the hydrophilic component.

In general, the continuous phase is of an elastic material while the discrete phase is generally of a plasatic material. By an "elastic" material is intended a polymer which can easily undergo relatively large, rapidly reversible, elongation. "Plastic" materials include those that are typically more rigid and relatively resistant to deformation.

In one embodiment, the hydrophilic material is PEO crosslinked with, e.g., a triisocyanate, while the hydrophobic material is polystyrene (pST) or poly(butyl methacrylate) (pBMA), crosslinked with a suitable crosslinking agent, e.g., ethylene glycol dimethacrylate (EGDMA), divinyl benzene (the system optionally including divinyl, diacrylic, and dimethacrylic monomers). As will be discussed in more detail, the weight ratio of PEO to pST or pBMA can be varied to alter release rate and the overall release profile, but typically the ratio of PEO to pST or pBMA is in the range of about 1:9 to 9:1, more typically in the range of about 4:6 to 6:4. In a preferred embodiment, the continuous phase is PEO, while the discrete phase is pST or pBMA.

In such an embodiment, organic, nonpolar solvents such as chloroform, benzene, toluene, methylene chloride, chlorobenzene, chlorotoluene, methyl ethyl ketone (MEK), cyclic aromatics, halogenated cyclic aromatics, and cyclohexane are suitable for loading drug into both domains, while more polar solvents such as water, acetone, ethanol, methanol or mixtures thereof are suitable for loading drug into the PEO domain preferentially.

In another embodiment, the hydrophobic component is PTMO and the hydrophilic component is poly(N,N'-diemthyl acrylamide (DMAA$_m$)-co-styrene), i.e., a copolymer of DMAA$_m$ and styrene, wherein crosslinking is again provided by, preferably, a triisocyanate for crosslinking PTMO and EGDMA for crosslinking DMAA$_m$ and ST. Typically, the ratio of PTMO to DMAA$_m$-co-styrene is in the range of about 1:9 to about 9:1, more typically in the range of about 4:6 to 6:4. Preferably, the continuous phase is PTMO and the discrete phase is DMAA$_m$-co-styrene.

In general, the following compounds are examples of suitable crosslinking agents for both the hydrophilic and hydrophobic components:

(1) triisocyanates, e.g.
 (a) 1,2,3-propanetriyl tris(3-isocyanato)-4-methyl carbanilate (PTIMC) and (b) 1,1,1-tris[N-(4'-methyl-3'-isocyanatophenyl) carbamoyl-oxymethyl]propane (TMIPCOP);

(2) reaction products of diisocyanates, e.g.

(a) reaction products of water and diisocyanates such as Biuret triisocyanate;

(b) reaction products obtained from trimerization of diisocyanates such as isocyanurate; and (c) (2-isocyanato) ethyl-(2,6-diisocyanato)hexanoate; and (3) triols used in conjunction with diisocyanates, e.g. triols such as trimethylol propane, trimethylol isobutante, and poly(ε-caprolactone triol), and diisocyanates such as 2,6-toluene diisocyanate (TDI), 4,4'-diphenylmethane diisocyanate (MDI), 1,6-hexamethylene diisocyanate (HDI), and 2,4-toluene diisocyanate cyclohexyl diisocyanate (CHDI).

In the latter case, i.e., where the hydrophobic component is PTMO and the hydrophilic component is DMAA$_m$-co-styrene, suitable solvents which can be used to load drug into both domains here include chloroform, methylene chloride, cyclic aromatics, and halogenated cyclic aromatics, while solvents that will load the PTMO domain preferentially include heptane, hexane, and halogenated linear alkanes. Solvents that will load the ST-DMAA$_m$ domain preferentially include water, methanol, ethanol, propanol, and acetone.

In either of the above-described embodiments, synthesis can be simultaneous or sequential, although simultaneous synthesis is preferred. In simultaneous synthesis, the selected monomers or prepolymers—i.e., polyethylene oxide or polytetramethylene oxide—are crosslinked with, for example, a triisocyanate to form a matrix, i.e., to form the "continuous phase", at the same time that the styrene, methacrylate, and dimethylacrylamides are polymerized and crosslinked with, e.g., EGDMA, to form the localized regions within the matrix. Alternaively, the matrix comprising the first material can be formed first, followed by sorption of monomer(s) or prepolymer(s) into the matrix and polymerization therein to give localized regions of the second material.

Synthesis of either the PEO or the PTMO networks is carried out by admixture of the selected amounts of prepolymers and crosslinking agent(s) in approximately a one-to-one functional group ratio, i.e., OH/NCO is about 1/1. The mixture is allowed to react in an inert atmosphere, e.g., under nitrogen, argon, or the like, at a temperature in the range of about 40° C. and 120° C., preferably in the range of about 60° C. and 65° C., for, preferably, at least about several days. The resulting polymeric matrix is purified by immersion in a selected solvent, i.e., one that is a good solvent for purifying the polymers of both phases, for example, water, ethanol, acetone, methanol, methylene chloride, and mixtures thereof.

In the alternative embodiment according to which the second material is sorbed into a preformed matrix of the first material, essentially the same reaction and purification conditions are used as described for the simultaneous polymerization.

Drug loading into the IPNs is effected by immersion of the dried matrices in a solution containing the drug, or, if the drug is a liquid, into the drug itself, neat or in admixture with a selected solvent. As noted above, the solvent chosen for drug loading plays a key role in determining into which of the two domains of the IPN the drug is loaded. The degree of drug loading (drug weight/polymer weight) can be approximated to be within a given range by the following relationships:

$$\text{lower limit: } \frac{W_s}{W_p} \times [\text{drug}] \rightarrow \text{solvent phase only}$$

$$\text{upper limit: } \left[\frac{W_s}{W_p} + K\right][\text{drug}] \rightarrow \text{solvent phase } +$$

polymer phase wherein K is the drug/polymer partition coefficient, Ws is the weight of absorbed solvent, and Wp is the weight of dried polymer.

An important advantage of the present invention is that the release rate and overall release profile of a drug incorporated into the IPN matrix may be controlled by selection of the materials used for domains A and B, the relative amounts of the materials present in the matrix, the diffusivities and solubilities of the drug in the materials, the solvent used to load drug, the degree of crosslinking, domain size, which domain is "the continuous phase" and which the "discrete phase", the size of the final device, and the hydrophilicity/hydrophobicity ratio of the drug loaded.

The following systems provide an illustration of how these various factors affect drug loading, release rate, and the overall release profile.

Case 1: The continuous phase is of a hydrophilic material, e.g., polyethylene oxide crosslinked with triisocyanate; the localized regions are of a hydrophobic material, e.g., polystyrene crosslinked with EGDMA. The matrix is loaded with a drug dissolved in chloroform, a good solvent for both the hydrophilic and hydrophobic materials. Thus, both domains are loaded with drug. In this case, the hydrophilic matrix serves to release drug initially and rapidly; the localized hydrophobic domains provide for gradual release even after the continuous phase has been depleted. FIG. 1 is a graph of the predicted release rate. The solid line represents drug release from the system just described while the dotted line represents drug release from a typical homo- or copolymer matrix. As FIG. 1 illustrates, the proposed IPN achieves a more gradual drop in release rate relative to a conventional first-order matrix, due to diffusion of the drug from the domain where the diffusivity is low into and through the depleted higher diffusivity domain.

Figure 2:
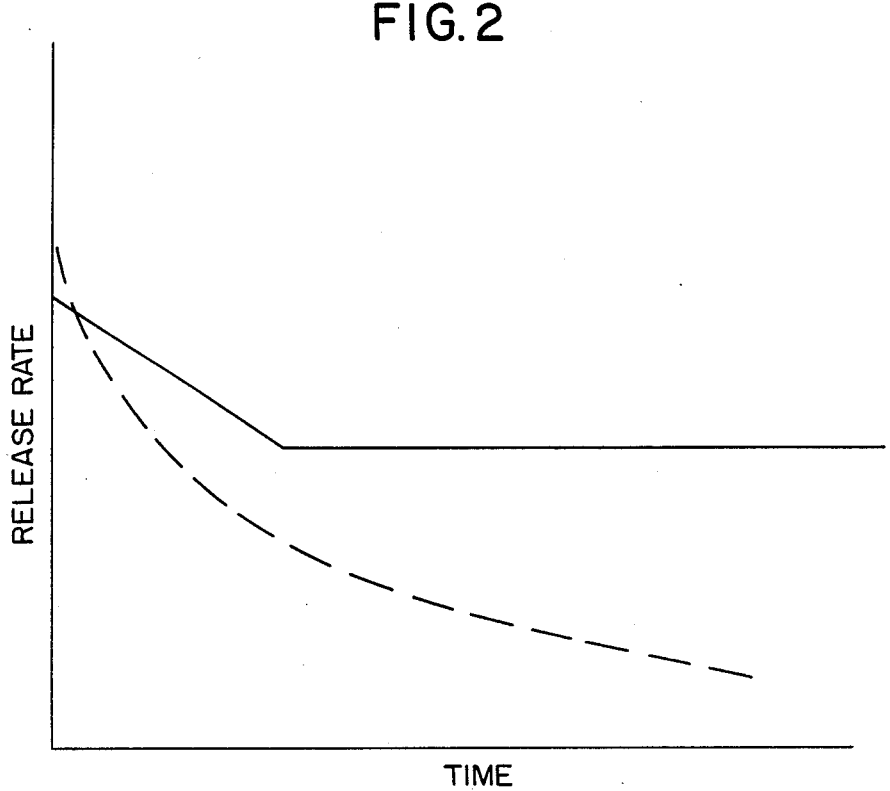
FIG. 2 is a graph showing the predicted release kinetics from the "Case 2" IPNs of the present invention.

Case 2: The continuous phase is hydrophobic, e.g., of PTMO; the localized regions are hydrophilic, e.g., P(DMAA$_m$-co-styrene). A solvent such as a water-ethanol mixture is selected so as to load drug into both domains. In this case, the PTMO will provide for initial and slow depletion of drug and subsequently will serve as a diffusional barrier layer to release from the localized hydrophilic domains. The P(DMAA$_m$-CO-ST) islands will serve as the drug reservoir. As illustrated in FIG. 2, which graphically shows the release rate over time from such a system (the solid line representing drug release from the Case 2 system, while the dotted line represents drug release, as before, from the typical zero-order release matrix), approximately zero order release is achieved when the localized regions become the "barrier" layer.

Figure 3:
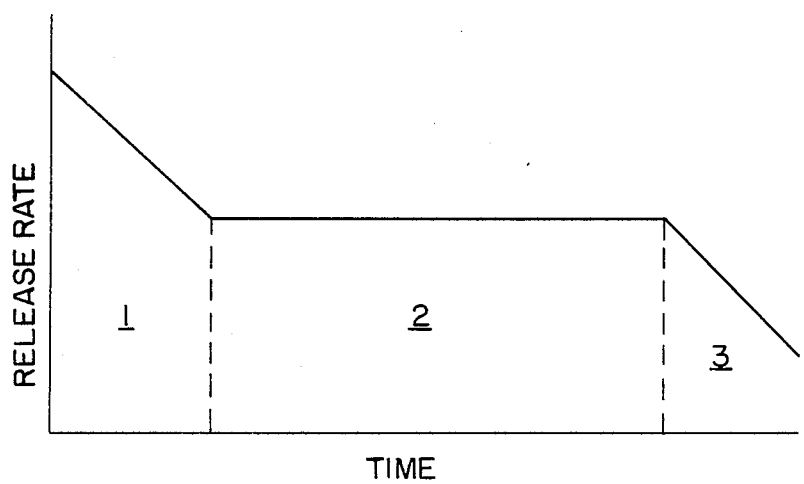
FIG. 3 is a graph showing the three phases of drug release from IPN matrices.
Figure 4:
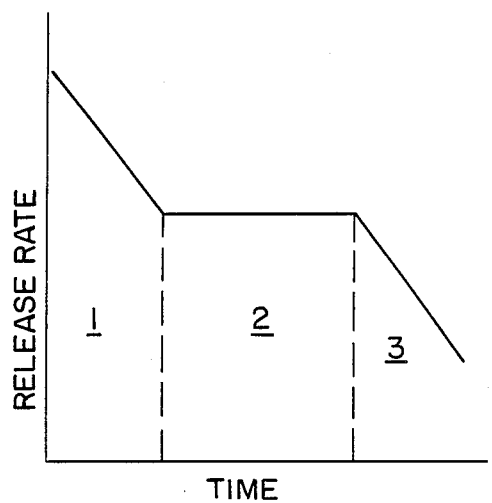
FIGS. 4 and 5 are graphs showing how the three phases of drug release vary depending on the size and hydrophobicity of the two IPN domains.
Figure 5:
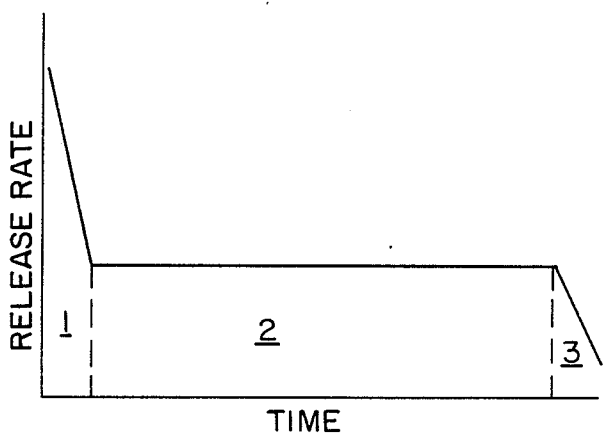

FIG. 3 shows the three main phases of a timed release profile: an initial high release rate, declining gradually (1); a flat, approximately "zero order" period over which the release rate remains substantially constant (2); and a gradual decline from the zero order value (3). In Case (2) systems, as illustrated by FIG. 4, a shorter zero order phase (portion (2) of the curve) will be obtained by introducing smaller hydrophilic regions or by choosing a material for the continuous matrix that is less hydrophobic. Conversely, as illustrated by FIG. 5, a longer zero order phase can be achieved by introducing larger hydrophilic regions or a more hydrophobic continuous matrix.

A drug burst effect may be obtained by choosing a material for the discrete phase which won't begin to release drug until after the matrix has been substantially depleted. Such a release profile is desirable, for example, when a higher blood concentration of drug is necessary after release has been approximately constant for some period of time.

Administration of the drug-loaded IPNs described herein can be via any of the accepted modes of administraion for the particular drug(s) administered. These modes of administration include oral, parenteral and otherwise systemic methods, e.g., via implants. Drugs may also be administered transdermally by applying the drug-loaded IPN to skin surface. The compositions include a conventional pharmaceutical carrier or excipient and, in addition, may include other medicinal agents, pharmaceutical agents, carriers, adjuvants, etc.

Conventional non-toxic carriers include, for example, pharmaceutical grades of mannitol, lactose, starch, magnesium stearate, sodium saccharin, talcum, cellulose, glucose, sucrose, magnesium carbonate, polyalkylene glycols, e.g., propylene glycol, and the like. For liquid pharmaceutically administerable compositions in particular, the IPN may be dispersed in a carrier such as, for example, water, saline, aqueous dextrose, glycerol, ethanol, and the like, to thereby form a suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Penn. The composition or formulation to be administered will, in any event, contain a quantity of drug in an amount effective to alleviate the symptoms of the subject being treated.

The following examples further illustrates the IPNs of the invention and the processes by which they may be prepared. These examples are not intended to limit the invention in any manner.

EXAMPLE 1

(a.) Waxy polyethylene oxide of nominal molecular weight 1000 was melted and kept at 60° C. under vacuum for one day to remove absorbed water. Five (5.0) g of vinyl monomer of styrene (ST) were purified by heating under a nitrogen atmosphere with vacuum, and the distillate at 57° C./35 mm Hg was collected. The following reaction components were then admixed with 10 ml double-distilled benzene at 60° C.: a trisocyanate crosslinking agent having the structure

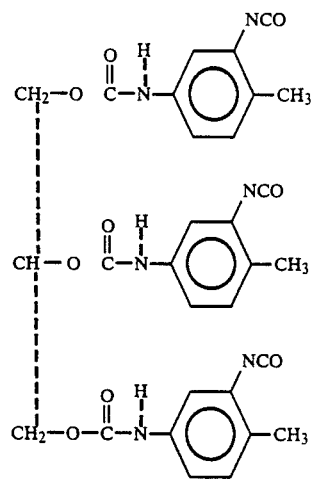

(1,2,3-propanetriyl tris (3-isocyanato)-4-methyl carbanilate) ("Tris-NCO"), 3.414 g, 66 wt. % in solid content in ethyl acetate; the purified styrene distillate, 5.0 g; 2,2'-azobisisobutyronitrile (AIBN), 0.0258 g; and ethylene glycol dimethacrylate (EGDMA), 0.045 g. Five (5.0) g of molten and dried PEO prepared as above was mixed with the other mixtures and poured into a three-neck, round-bottom flask which was preheated in an oil bath at 65° C.±2° C. The round-bottom flask was equipped with a reflux condenser, thermometer, nitrogen inlet and magnetic stirrer. The simultaneous reactions of crosslinking of vinyl monomer and prepolymer proceeded until the solution became opaque and increased viscosity of solution restricted the movement of the magnetic stirring bar. The viscous solution was injected into glass tubes and degassed at 60° C. under vacuum for about one minute. The tube was sealed with a cork stopper and Teflon tape and kept for postpolymerization in an air-circulating oven at 60° C. for 5 days. The cured polymers were separated from the glass tubes by breaking the glass and soaking in water for one week. The polymer was then cut into disk-shaped pieces. All of the unreacted components and the benzene were extracted in an excess of chloroform for 10 days, changing the chloroform solution every two days. The swollen disks were transferred in chloroform into a water-ethanol mixture (50/50 v/v) for seven days to replace the chloroform. They were then maintained in ethanol for two days. The purified polymers were dried at room temperature in open air for one day and then under vacuum for four days. The dried polymers were kept in a sealed bottle.

(b.) The procedure of Example 1 was repeated using 7.5 g PEO; 5.122 g Tri-NCO; 2.5 g styrene distillate; 0.028 g AIBN; and 0.0226 ml EGDMA. Prepolymerization treatment—i.e., treatment prior to during—was carried out for 10.0 rather than 7.5 hours.

EXAMPLE 2

(a.) An HTIPN was prepared from PEO and n-butyl methacrylate, using substantially the same procedure as in Example 1(a). In place of styrene, n-butyl methacrylate (BMA) was purified by heating under nitrogen, and the distillate at 50° C./3 mm Hg was collected.

The following amounts of the various reaction components were used here: 5.0 g PEO; 3.414 g Tri-NCO; 5.0 g BMA; 0.0258 g AIBN; and 0.0332 ml EGDMA.

Prepolymerization treatment was carried out at 65° C. for 5.5 hours, while postpolymerization was carried out at 60° c. for 4 days.

(b.) The procedure of part (a) of this Example was repeated using: 2.5 g PEO; 5.122 g Tri-NCO; 2.5 g BMA; 0.0258 g AIBN; and 0.0166 ml EGDMA. Prepolymization treatment at 65° c. was carried out for 6.0 hours.

EXAMPLE 3

(a.) An HTIPN of polytetramethylene oxide (PTMO) and N,N'-dimethylacrylamide ($DMAA_m$) and styrene was prepared as follows. 3.4 g PTMO of nominal molecular weight 1000 (avg. OH 112) was dried at 80° C. under vacuum for 6 hours. $DMAA_m$ (2.5 g) and ST (2.5 g) were distilled under nitrogen atmoshpere with reduced pressure as in Example 1. The PTMO, ST and $DMAA_m$, along with 2.125 g TRI-NCO, 0.013 g AIBN, and 0.0425 ml EGDMA were mixed and bubbled with dry nitrogen for 20 minutes. The resulting oxygen-free mixture was injected into a membrane mold composed of Mylar ® sheets using a rubber gasket as a spacer. In order to cure and crosslink the polymer mixture, the mold was maintained at 60° C. for 4 days. The polymer membrane was separated from the mold and soaked in excess methanol for one week, followed by swelling in a methanol/water mixture (1:1 by volume). The swollen polymer was cut into a circular disk and dried under vacuum for 4 days.

(b.) An HTIPN of polytetramethylene oxide (PTMO) and N,N'-diemthylacrylamide co-styrene was prepared substantially according to the procedure of part (a.) of this Example, with the following components and proportions: 3.4 g PTMO; 2.125 g Tri-NCO; 2.0 g $DMAA_m$; 3.0 g styrene; 0.013 g AIBN; and 0.0440 ml EGDMA.

(c.) An HTIPN of polytetramethylene oxide (PTMO) and N,N'-diemethylacrylamide co-styrene was prepared substantially according to the procedure of part (a.) of this Example, with the following components and proportions: 3.4 g PTMO; 2.125 g Tri-NCO; 1.5 g $DMAA_m$; 3.5 g styrene; 0.013 g AIBN; and 0.0450 ml EGDMA.

(d.) An HTIPN of polytetramethylene oxide (PTMO) and N,N'-dimethylacrylamide co-styrene ($DMAA_m$) was prepared substantially according to the procedure of part (a.) of this Example, with the following components and proportions: 3.4 g PTMO; 2.125 g Tri-NCO; 1.0 g $DMAA_m$; 4.0 g styrene; 0.013 g AIBN; and 0.0458 ml EGDMA.

EXAMPLE 4

Indomethacin was loaded into the hydrophilic (PEO) and/or the hydrophobic (ST or BMA) domains of the HTIPNs of Examples 1(a), 1(b), 2(a) and 2(b), as follows: Disk-shaped devices of the four HTIPNs of Examples 1 and 2, 9.0±0.5 mm in diameter and 2.3±0.1 mm in thickness (in the dried state), were equilibrated with an excess of an ethanol-chloroform mixture to extract all the unreacted ingredients. The ratio of ethanol to chloroform in the extraction mixture was varied from a chloroform-rich composition to an ethanol-rich composition to reduce the size of swollen disk gradually before drying—i.e., 100% $CHCl_3$ (2 day extraction), 80/20 $CHCl_3$/EtOH (2 day extraction), 50/50 $CHCl_3$/EtOH (1 day extraction), 20/80 $CHCl_3$/EtOH (1 day extraction), 100% EtOH (1 day extraction). The drug solution was provided having a concentration of 10 mg/ml in a water-acetone mixture (40 vol. % of water). The water-acetone mixture was chosen as the drug carrier for loading in order to load drug into the PEO phase predominantly, since the mixture is a good solvent for PEO but a poor solvent for polystyrene and poly(n-butyl methacrylate). After maintaining the devices in the drug solution at room temperature for 3 days, the drug-loaded devices were removed from the drug solution and cooled in a dry ice chamber, dried at −20° C. under vacuum for 1 day, followed by drying at room temperature for 2 days. This procedure was designed to prevent drug migration to the polymer surface due to low drug solubility and low drug diffusion coefficient at low temperature. The drug content of the four HTIPN disks was as follows: HTIPN of Example 1(a), 5.1 wt. %; HTIPN of Example 1(b), 6.1 wt. %; HTIPN of Example 2(a) 5.8 wt. %; and the HTIPN of Example 2(b), 5.9 wt. %. Drug loading content was measured by weight.

EXAMPLE 5

Progesterone was loaded into the HTIPN of Example 1(a) as follows. Five disk-shaped devices of the HTIPN of Example 1(a), 8.7±0.1 mm in diameter and 1.5±0.1 mm in thickness, were allowed to absorb progesterone solutions in chloroform, the drug concentration of which varied from 15 mg/ml to 60 mg/ml (see Table 1). Chloroform was selected as a good solvent for both the hydrophilic and the hydrophobic phases.

The drug loading content was controlled as follows. All the drug solution was absorbed into the polymer matrix because the quantity of solution was less than the maximum which could be absorbed at equilibrium. As a result, all the drug in solution was also incorporated into the device and a partitioning effect in the complete equilibrium state, during drug loading, was thus avoided.

All of the drug dissolved in a solvent can, by the foregoing method, be absorbed into both phases and equilibrated throughout the polmer matrix until there is no concentration gradient within the device. After absorption of solution for 1 week, the highly swollen devices were cooled between two pieces of dry ice followed by evaporation of the solvent, on the dry ice, for 18 hours. The rapid evaporation rate of chloroform at room temperature easily induces the disintegration of devices due to the build up of stress between dried surface and swollen bulk phase. Thus, the above cooling step was effective to prevent drug migration and cracking of devices. After evaporation of solvent, the devcies were dried at room temperature for 2 days. Drug loading was evaluated by measuring weight after drying and is summarized in Table 1.

TABLE 1

| Sample | Wp* | Concentration of solution | Drug Content after loading |
|---|---|---|---|
| #1 | 0.1087 g | 15 mg/0.9 ml | 10.6 wt. % |
| #2 | 0.1114 g | 20 mg/0.9 ml | 14.5 wt. % |
| #3 | 0.1114 g | * 30 mg/0.9 ml | 18.6 wt. % |
| #4 | 0.1217 g | 40 mg/0.9 ml | 24.5 wt. % |
| #5 | 0.1163 g | 50 mg/0.9 ml | 35.1 wt. % |

*The weight of sample in the dried state before absorption of solution.

EXAMPLE 6

Sodium salicylate was loaded into the four HTIPNs of Example 3, as follows: Four disk-shaped devices formed from the HTIPNs of Example 3, 11.3 to 12.8 mm in diameter and 1.4±0.1 mm in thickness, in the dried state, were equilibrated with an excess amount of sodium salicylate solution for 4 days. The drug solution was 20 wt./vol. % sodium salicylate in a water-ethanol mixture (20 vol./vol. % water). The drug-loaded gels were dried at room temperature under vacuum for 5 days.

Drug loading in the devices was evaluated by measuring weight after drying and may be summarized as follows: (1) HTIPNs of Example 3(a), 39%; (2) HTIPN of Example 3(b), 35% (3) HTIPN of Example 3(c), 29%; and (4) HTIPNs of Example 3(d), 20%.

EXAMPLE 7

Drug release from the drug-loaded IPNs of Examples 4, 5 and 6 is evaluated as follows: From the equation $$\ln \frac{D_m}{D_o} \alpha \frac{Bq}{V_f}\left[\frac{1}{H} - 1\right] \qquad (2)$$

(Yasuda et al., *Die Macromolecular Chemie*, 126, 177, 1969), where $D_m$ and $D_o$ are the drug diffusion coefficients in swollen membrane and bulk water, respectively, Bq is the proportional constant to solute cross-sectional area, and $V_f$ is the volume of swollen membrane. It may be deduced that $$\frac{Bq}{V_f}$$

is proportional to $$\frac{1}{r^2}$$

where r is the radius of the molecule and H is the hydration of the hydrogel. Thus, drug release can be predicted based on aqueous swelling of the devices. From the above equations, it will be seen that as hydration rate doubles, the diffusion rate increases 10 times, while the flux of drug out of the device is proportional to both degree of loading and aqueous diffusion.

Figure 6:
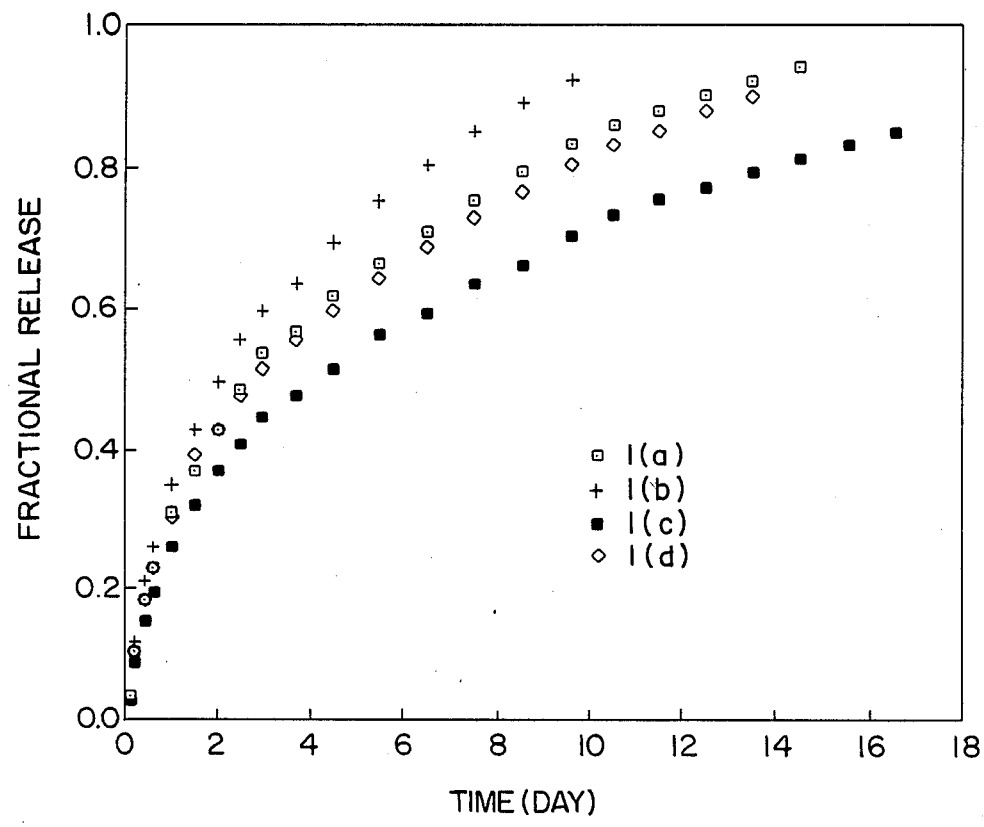
FIG. 6 is a graph showing the fractional release of indomethacin over time from the IPNs of Example 4.
Figure 7:
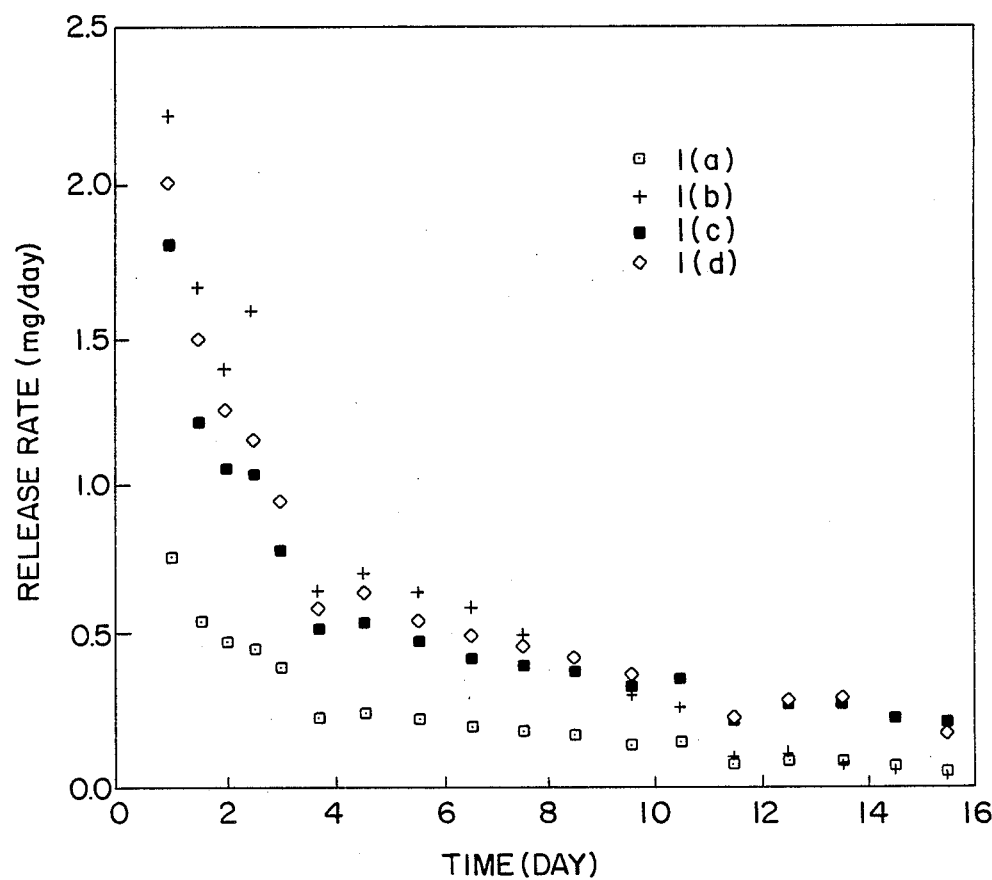
FIG. 7 is a graph showing the release rate of iNdomethacin over time, using the IPNs of Example 4.

Using the aforementioned relationships, the fractional release over time of indomethacin from the HTIPN disks of Example 4 was calculated and is plotted in FIG. 6. The release rate of drug from the same disks was experimentally determined and is plotted in FIG. 7. Release rate was highest for the HTIPN of Example 1(b), where water content was highest (about 40%), while release rate was lowest for the HTIPN of Example 1(a), where water content was lowest (about 10%). As expected, then, release rate was found to depend strongly on the equilibrium water content.

Figure 8:
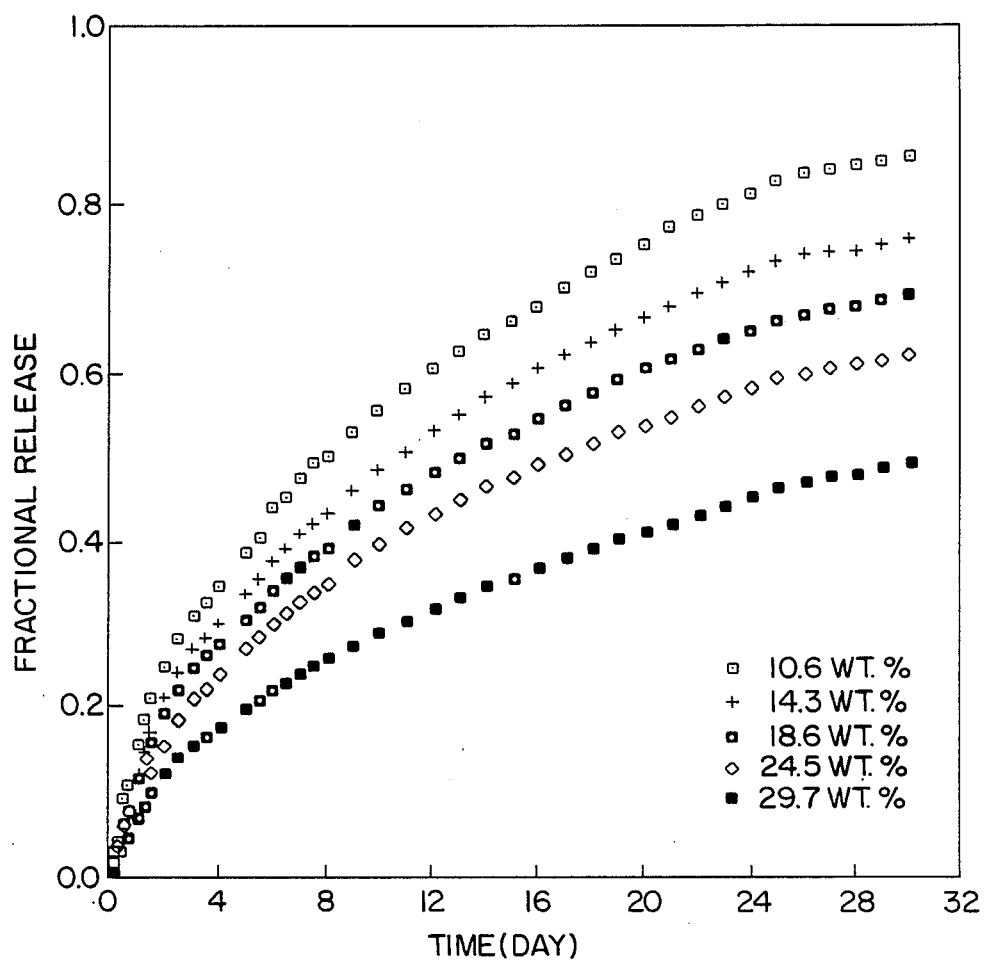
FIG. 8 is a graph showing the fractional release of progesterone over time from the IPNs of Example 5.
Figure 9:
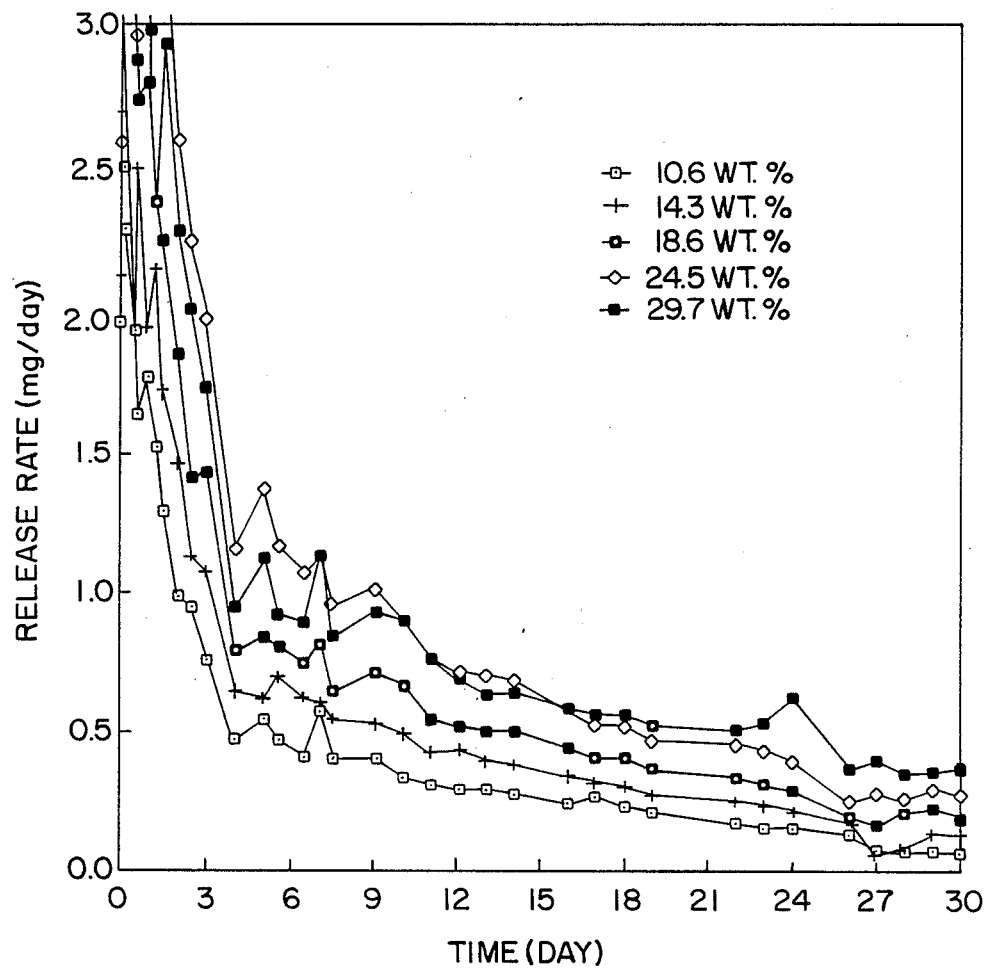
FIG. 9 is a graph showing the release rate of progesterone over time, using the IPNs of Example 5.

FIGS. 8 and 9, similarly, show the fractional release and release rate of progesterone from the HTIPN disk of Example 5.

Both the indomethacin- and progesterone-loaded disks show pseudo zero order kinetics in a device where the hydrophilic, PEO matrix provides for the initial, fast depletion of drug and the discrete hydrophobic styrene or BMA domains give slow drug release.

Figure 10:
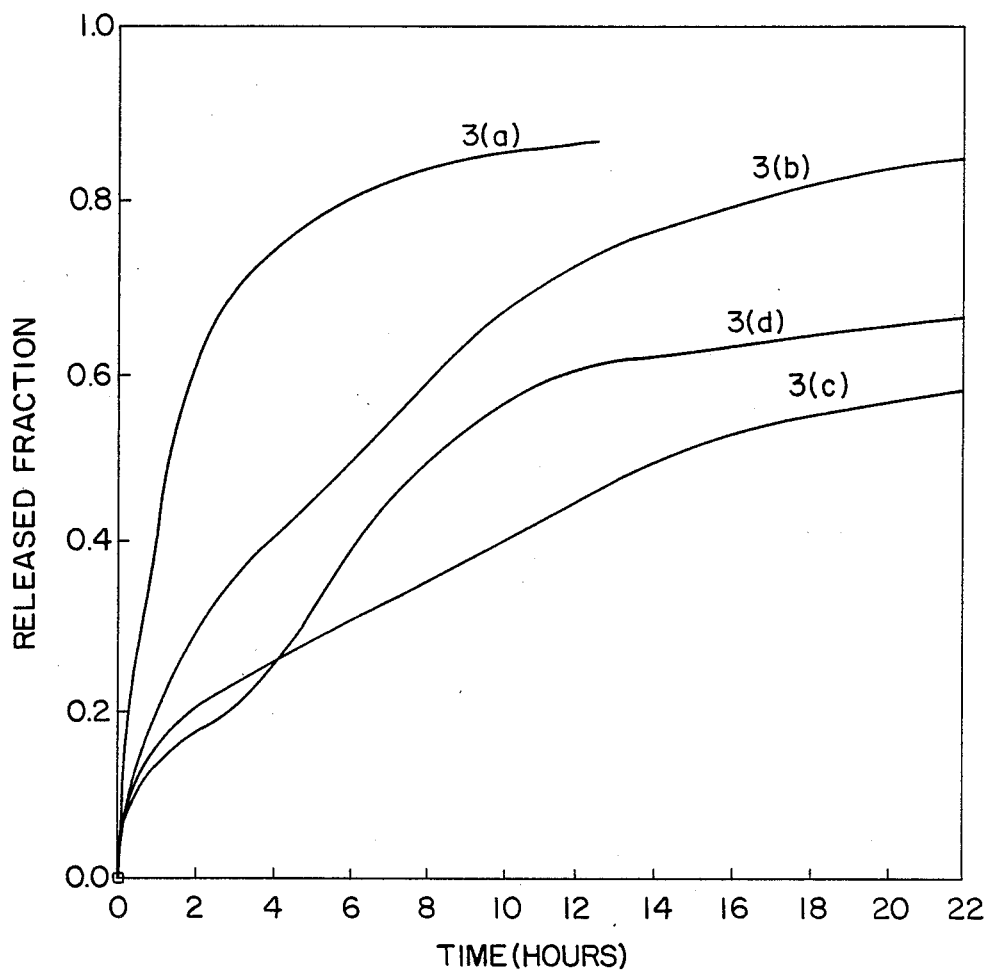
FIG. 10 is a graph showing the fractional release of sodium salicylate over time from the IPNs of Example 6.
Figure 11:
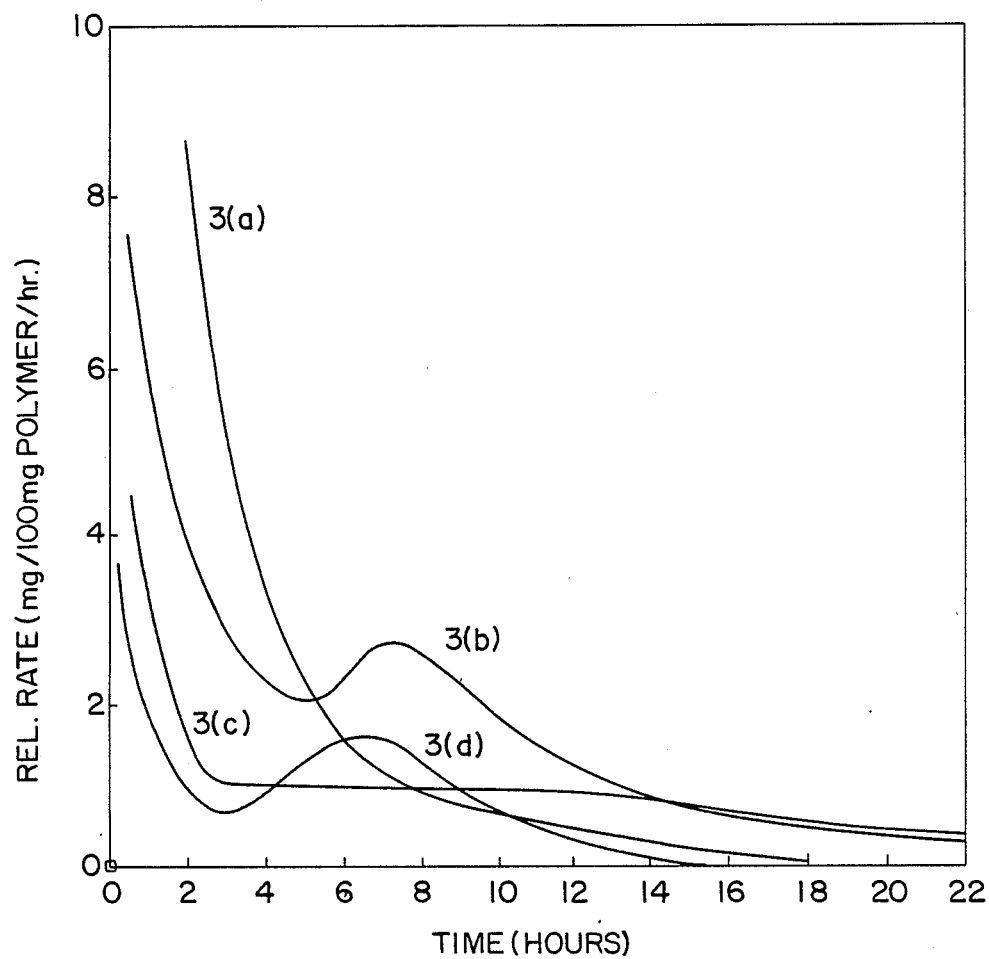
FIG. 11 is a graph showing the release rate of sodium salicylate over time, using the IPNs of Example 6.

FIGS. 10 amd 11 show the fractional release and release rate of sodium salicylate from the HTIPN disks of Example 6. The plots show approximately zero order release for the case where the hydrophobic PTMO matrix provides, initially, for the slow depletion of drug and subsequently, serves as a diffusional barrier layer. The localized hydrophilic $DMAA_m$/ST regions serve as the primary drug reservoirs, responsible for the burst effect noted with the HTIPNs of Examples 3(b) and 3(d).

In this example, drug release was monitored by UV spectroscopy: indomethacin at 266 nm, progesterone at 248 nm, and sodium salicylate at 280 nm. Sodium salicylate release rate was monitored continuously through the flow cell.

We claim:

1. A three-dimensional interpenetrating polymer network (IPN) for the substantially continuous release of a drug contained therein, comprising:
    (a) a continuous matrix of a first, crosslinked polymeric material;
    (b) localized regions of a second, crosslinked polymeric material dispersed throughout said matrix, wherein one of said polymeric materials is hydrophilic and the other of said materials is hydrophobic; and
    (c) a drug either dissolved or dispersed in one or both of said polymeric materials.

2. The IPN of claim 1, wherein said first material is hydrophilic and said second material is hydrophobic.

3. The IPN of claim 1, wherein said first material is hydrophobic and said second material is hydrophilic.

4. The IPN of claim 1, wherein the diffusivity $D_1$ of the drug in said first material is different than the diffusivity $D_2$ of the drug in said second material.

5. The IPN of claim 1, wherein the solubility $S_1$ of the drug in said first material is different than the solubility $S_2$ of the drug in said second material.

6. The IPN of claim 1, wherein the weight ratio of said first material to said second material is in the range of about 9:1 to about 1:4.

7. The IPN of claim 1, wherein said weight ratio is in the range of about 6:4 to about 4:6.

8. The IPN of claim 1, wherein only one of said first and said second materials contain a drug.

9. The IPN of claim 1, wherein both of said first and second materials contain drug.

10. The IPN of claim 9, wherein said first material contains a first drug and said second material contains a second drug.

11. The IPN of claim 1, wherein the hydrophilic material is polyethylene oxide crosslinked with a triisocyanate and the hydrophobic material is polystyrene or poly(butyl methacrylate) crosslinked with ethylene glycol dimethacrylate.

12. The IPN of claim 1, wherein the hydrophilic material is poly(N,N'-dimethyl acrylamide co-styrene) and the hydrophobic material is polytetramethylene ether glycol.

13. A method for making an interpenetrating polymer network (IPN) for the substantially continuous release of a drug contained therein, comprising:
    polymerizing and crosslinking a first component to give a continuous matrix of a first, crosslinked polymeric material;
    polymerizing and crosslinking a second component to give an IPN having localized regions of a second, crosslinked polymeric material within said matrix,
    wherein one of said first and said second materials is hydrophobic and the other of said materials is hydrophilic; and
    incorporating drug into the IPN by immersion in a drug solution.

* * * * *